United States Patent [19]

Vasta-Russell et al.

[11] Patent Number: 5,074,980
[45] Date of Patent: Dec. 24, 1991

[54] METHOD OF CHARACTERIZING POLYNUCLEOTIDES

[75] Inventors: Julia F. Vasta-Russell; Leslie E. Sachau, both of Wilmington; Deborah L. Freerksen, Hockessin, all of Del.

[73] Assignee: E. I. Du Pont de Nemours and Company, Wilmington, Del.

[21] Appl. No.: 442,673

[22] Filed: Nov. 29, 1989

[51] Int. Cl.$^5$ .......................... C25B 1/00; B01D 62/42
[52] U.S. Cl. ............................ 204/182.8; 204/299 R; 435/6
[58] Field of Search ........................ 204/299 R, 187.8; 435/6

[56] References Cited

PUBLICATIONS

Carter, W. A., Pitha, P. M., Marshall, L. W., Tazawa, I., Tazawa, S., and Ts'o, P. O., (1972), J. Mol. Biol. 70, pp. 567–587.
Carter, W. A., O'Malley, J. A., Beeson, M., Cunnington, P., Kelvin, A., Vere-Hodge, A., Alderfer, J. L., and Ts'o, P. O. (1976), Molecular Pharmacology 12, pp. 440–453.
Ts'o, P. O. P., Alderfer, J. L., Levey, J., Marshall, L. W., O'Malley, J. A., Horozewicz, J. S., and Carter, W. A. (1975), Molecular Pharmacology 12, pp. 299–312.
Greene, J. J., Alderfer, J. L., Tazawa, I. L., Tazawa, S., Ts'o, P. O., O'Malley, J. A., Carter, W. A. (1978), Biochemistry 17, pp. 4214–4220.
Freeman et al., Analytical Biochemistry 158, pp. 119–129 (1986).
Kohn et al., Analytical Biochemistry, 154, pp. 485–491 (1986).
Bindels et al., Journal of Chromatography, 252, pp. 255–267 (1982).

Primary Examiner—John Niebling
Assistant Examiner—Caroline Koestner

[57] ABSTRACT

Polydispersed, double-stranded and single-stranded polynucleotides are characterized according to their molecular size distribution. The polynucleotides are electrophoresed, stained, imaged and the image scanned and converted to pixel-by-pixel representations of the image density and size. The number and weight average molecular size are calculated along with the Z average molecular size.

11 Claims, 3 Drawing Sheets

METHOD OF CHARACTERIZING POLYNUCLEOTIDES

BACKGROUND OF THE INVENTION

This invention relates to a method of characterizing polynucleotides.

It is often necessary to characterize polynucleotides for quality control or other purposes. This is particularly necessary when polynucleotides are manufactured and some degree of consistency must be maintained between batches and the overall characteristics of the polynucleotide must be ascertained simply to verify that the product produced is that desired. The manufacture of polynucleotides is well known. For example, techniques for the manufacture of ssRNA are described in Carter, W. A., Pitha, P. M., Marshall, L. W., Tazawa, I., Tazawa, S., and Ts'o, P. O., (1972) *J. Mol. Biol.* 70, 567-587; Carter, W. A., O'Malley, J. A., Beeson, M., Cunnington, P., Kelvin, A., VereHodge, A., Alderfer, J. L., and Ts'o, P. O. (1976) *Molecular Pharmacology* 12, 440-453; Ts'o, P. O. P., Alderfer, J. L., Levy, J., Marshall, L. W., O'Malley, J. A., Horoszewicz, J. S., and Carter, W. A. (1976) *Molecular Pharmacology* 12, 299-312; and Greene, J. J., Alderfer, J. L., Tazawa, I., Tazawa, S., Ts'o, P. O., O'Malley, J. A., Carter, W. A. (1978) *Biochemistry* 17, 4214-4220.

Current techniques available to analyze polymers included gel electrophoresis and size exclusion chromatography (SEC). Size exclusion chromatography, although commonly used in typical polymer analysis, was limited in its inability to retain molecules beyond 1,000,000 molecular weight, and this was unsuitable for the polynucleotide application. A further limitation of this method involves the shearing of large molecules when forced at high pressure through column packings of limited pore size. Consequently, erroneous sizing of molecules occurs in the size distribution from molecular breakdown.

Gel electrophoresis, using agarose as the gel matrix has proved to be an extremely suitable technique for characterizing the entire size distribution range of biopolymers having high molecular weights. The concentration of the gel matrix was easily adjusted to accommodate the extensive range of size distribution. After electrophoresis, the gels were scanned by laser densitometry, however, no method existed to convert the densitometry data into size distribution parameters. Current software generally is limited to quantitation of discreet bands of nucleic acids and not size distribution type analyses.

Hence, current techniques have not been entirely satisfactory for the purpose of characterizing polydispersed polynucleotide size distributions.

Freeman, et al. in their article appearing in *Analytical Biochemistry* 158, 119-129 (1986) describe a technique for characterizing DNA by quantitating the molecular size distribution by determining strand breaks in deoxyribonucleic acid (DNA). Freeman, et al. disclose only a very rudimentary system involving determining number average molecular lengths and length average molecular lengths of DNA by using rather the mobilities of the molecular length standards. This is too rudimentary and crude to provide a valuable analysis tool.

Kohen et al., *Analytical Biochemistry*, 154, 485-491 (1986) describe a technique for determining number average molecular weight by measuring absorbance to ascertain single strand breaks. Kohen et al. apparently do not determine weight average molecular weight, Z average molecular size, polydispersity or skewness.

Bindels et al. in *Journal of Chromatography*, 252; 255-267 (1982) describe a technique of using high performance gel permeation chromatography to determine the weight average and number average molecular weights for certain materials. A disadvantage of such a chromatographic technique has been discussed above.

SUMARY OF THE INVENTION

Many of the disadvantages of these prior art techniques are overcome by the method of this invention in which densitometry data derived from an electrophoresis gel is resolved into size distribution data derived from classical polymer chemistry parameters of number average molecular size, weight average molecular size, Z average molecular size, polydispersity, and skewness.

This invention provides a method of characterizing polydispersed, single-stranded or double-stranded polynucleotides according to this molecular size distribution comprising the steps of converting the polynucleotide to single stranded polynucleotides, electrophoresing the single stranded polynucleotides in a lane of a gel, staining the electrophoresed polynucleotides, forming an image having an absorbance distribution proportional to the concentration of stained polynucleotides, scanning the image of the gel lane to the electrophoresed polynucleotides into pixel-by-pixel representations of the absorbance $A_i$ distribution of the electrophoresed polynucleotides, in terms of absorbance $A_i$ and size $S_i$, calculating the number average molecular size $S_n$ of the polynucleotides distribution by the formula $$\overline{S_n} = \Sigma A_i / \Sigma A_i / S_i$$

calculating the weight average molecular size $S_w$ of the polynucleotides distribution by the formula $$\overline{S_w} = \Sigma A_i\, S_i / \Sigma A_i$$

calculating the Z average molecular size $S_z$ of the polynucleotides distribution by the formula $$\overline{S_z} = \Sigma A_i\, S_i^2 / \Sigma A_i\, S_i$$

thereby to characterize the polynucleotide by the criteria number average molecular size, weight average molecular size, and Z average molecular size.

In addition, the polydispersity and skewness may be calculated to further characterize the polymer.

In preferred embodiments of the method, the additional step is included of including a blank lane (i.e., a lane not containing and polynucleotide sample) alongside the the lane containing sample polynucleotide in the gel, scanning the blank lane to obtain pixel-by-pixel representations of the absorbance of the blank lane and subtracting pixel-by-pixel the absorbance of the blank lane from that of the electrophoresed lane before calculating.

In a further improved embodiment of the invention the additional step is included in including a blank lane on either side the polynucleotide-containing lane, scanning the blank lanes to obtain pixel-by-pixel representations of absorbance of each blank lane, and subtracting pixel-by-pixel the absorbance of the average of the blank lanes from that of the electrophoresed lane before calculating.

This technology has been successfully applied during the development work for potential pharmaceuticals comprising a mixture of homopolymeric and heteropolymeric ribonucleic acids. The enzyme polynucleotide phosphorylase produces a broad size distribution of single-stranded ribonucleic acids. The biopolymers that were made ranged from 100 to 100,000 nucleotide bases in length or approximately 25,000 to 2,500,000 molecular weight. The size distribution can be thoroughly described in terms of number average, weight average, and Z average molecular size, plus polydispersity and skewness.

Number average molecular weight can be determined reasonably accurately without subtracting the baseline, but weight average, Z average, polydispersity, and skewness can not. The method of the procedure provides one with the ability to calculate the real weight average etc. by first subtracting the baseline, regardless of whether it increases, decreases, or is variable for some other reason. Additionally, an accurate calculation is made possible only by employing a curvesmoothing function.

A critical need is to determine if changes in the process and or purification conditions affect the product. Thus, it is necessary to be able to thoroughly and reproducibly characterize such polymers to measure what, if any, changes have occurred. Further, such a technique would also be useful in routine quality control analysis of production lots.

BRIEF DESCRIPTION OF THE DRAWINGS

The invention may perhaps be better understood by consideration of the following drawings wherein like elements have been given similar reference numerals in which.

DESCRIPTION OF THE PREFERRED EMBODIMENT

The method of this invention operates in conjunction with a suitable data acquisition system and laser densitometer. In the preferred embodiment, the LKB data acquisition and analysis system is used to operate on a microcomputer 10 and interfaces with an LKB Produkter AB, (LKB) 2222-020 Ultro-Scan XL Laser Densitometer. The microcomputer 10 interfaces with a number of peripheral units 12 and a software for the system 14. The microcomputer 10 receives input directly from the laser densitometer 16 via an RS-232C data communication line. Once the data has been received by the system it can be processed and analyzed.

FLOW CHART

Figure 1:
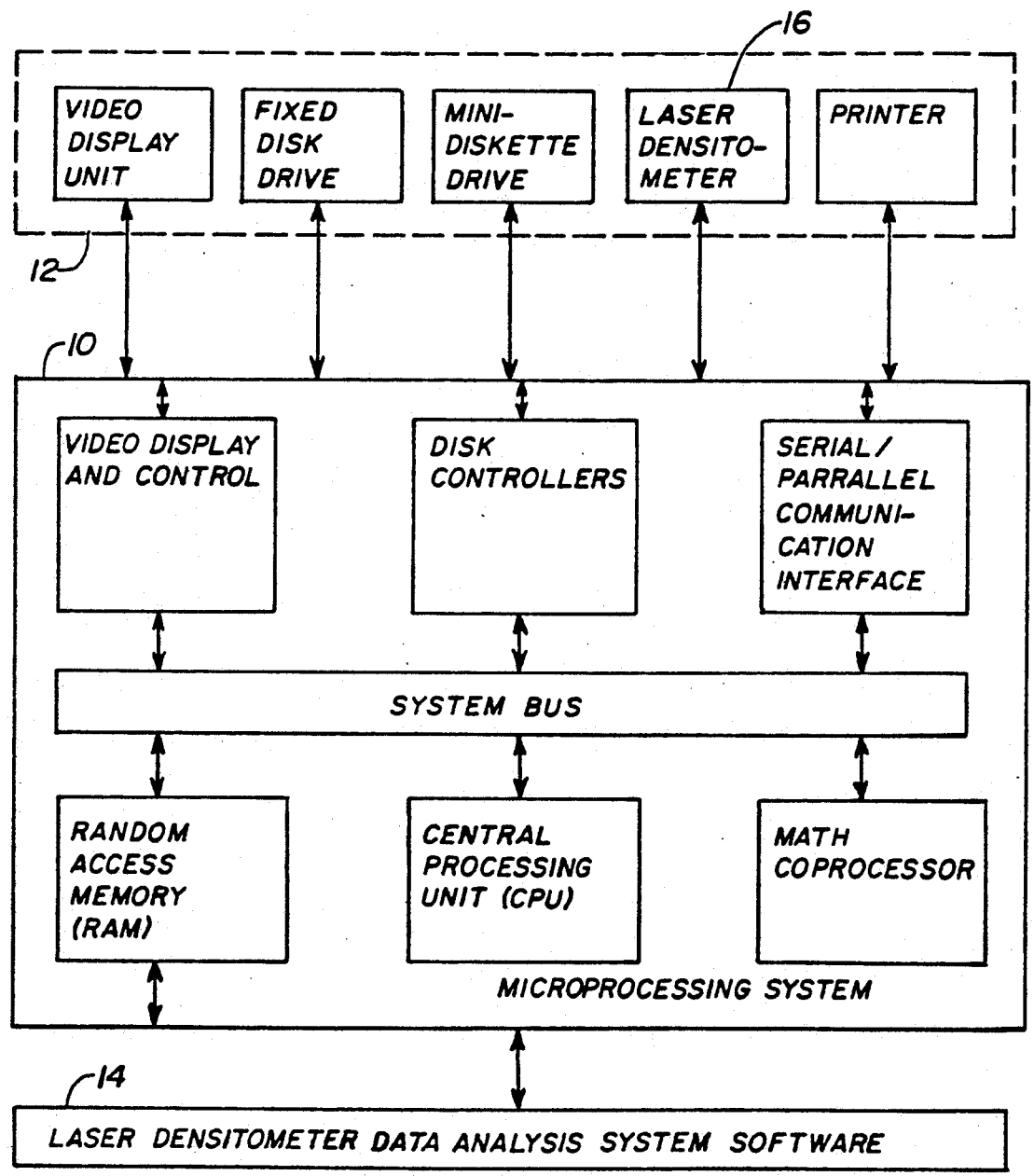
FIG. 1 is a block diagram of the densitometer and data acquisition system used in connection with the method of this invention.
Figure 2:
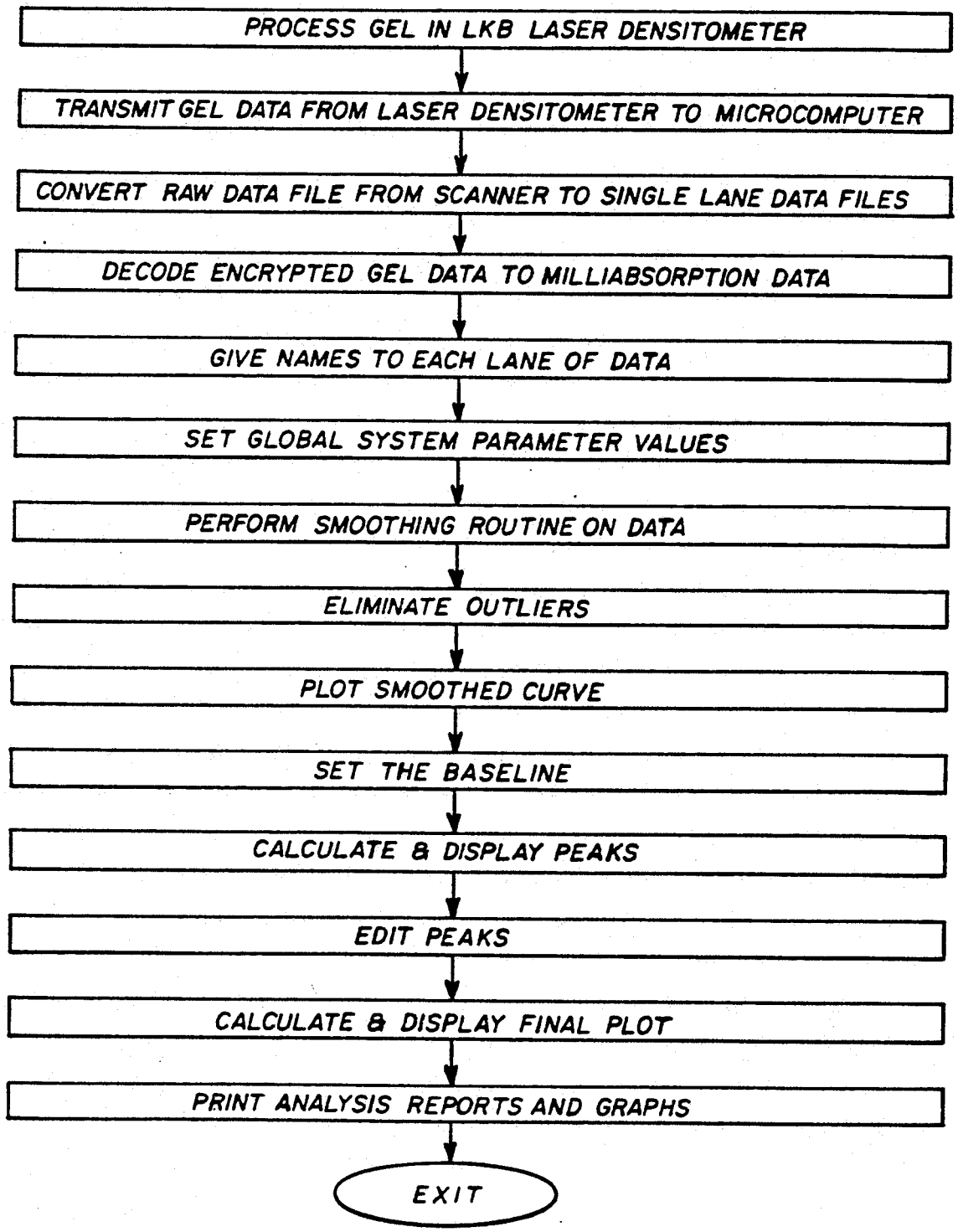
FIG. 2 is a flow diagram of the method of this invention.
Figure 3:
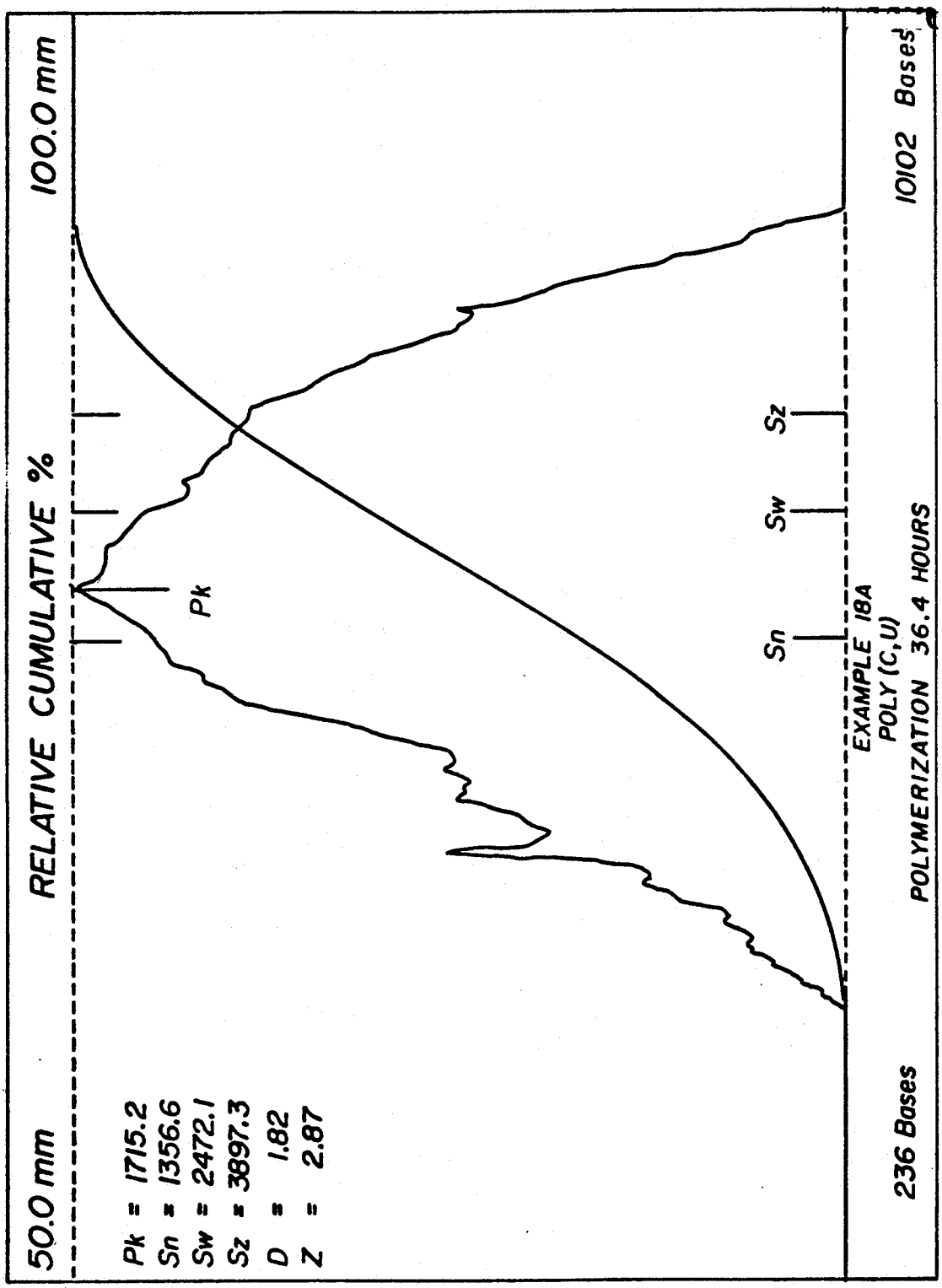
FIG. 3 is a representative standard curve describing the results that are available using the method of this invention.

The flow chart shown in FIG. 2 depicts the process for acquiring and analyzing the data. The system software is comprised of six primary functional modules: utilities, data capture, data decoding, data description, data analysis and data reporting. The utilities module provides the user with a means of defining global system variables. As input to this module, the user may enter outlier sensitivity data, blank lane subtraction information, as well as the colors that the system will display. The output of this module are the global system parameters available to all other modules.

The data capture module accepts as input, data transmitted directly from the laser densitometer via RS-232C serial communication lines. The data that is transmitted is a stream of encoded ASCII characters that represent milliabsorption units. The output of this module is a data file.

The data description module provides the user with the capability to name and store each lane of data transmitted from the laser densitometer. Each lane of data is broken out into individual files. The files are named and stored on a fixed disk drive on the microcomputer.

Each of these files is then decoded. That is, the data that was encoded in the data transfer from the laser densitometer is converted to ASCII and stored in files. After the data has been received from the laser densitometer, preprocessed and stored in files, it can be analyzed. The analysis process has four major functional components.

The data is first read from the stored files into an array in the computer. The data in the array represent milliabsorption units. The data is then smoothed. A relatively simple smoothing algorithm is used to smooth the data. Two steps are involved in the procedure. First, the data in the array window (the data array window value is an integer constant imbedded in the code which represents the number of array elements included in the average) is averaged. As the window is moved element by element through the entire array, and the average value calculated, it is assigned to array element n/2. N is defined as the data window size constant whose value is provided as an input to this module.

Next, the data in the array is analyzed to see if there are outliers. If there are, they are eliminated. Outlier detection is controlled by the global system parameter "outlier sensitivity" defined in the utilities module. All outlier information is stored in a data file. In order to eliminate outliers, their values must be identified and a suitable replacement value calculated. The following four processes perform these functions.

Every value in the data file array is processed to determine if it deviates significantly from the previous value in the array. The significance level is determined by the global parameter "outlier sensitivity" defined in the utilities module. If there should be a significant increase or decrease, the position of the outlier is stored to a variable. This variable represents the output of the module.

The outlier position index in the data array is then translated to a millimeter value using the following formula:

$$MMPos = IndexValue * Ystep$$

Ystep is the value describing the ratio of X to Y.

If an outlier is found, its value is replaced by an average value calculated as the average value in the data window. The data window is defined by a data window constant. For example, if the data window (DW) is defined as 10, and the outlier is in position 20 of the array, the outlier is replaced with the value of:

$$Y(I) = \frac{\Sigma_{i=1,20} Y}{10}$$

The output of this module is the data array with all outliers replaced.

After finding and eliminating the outliers, the data points are then plotted on the screen using the general X, Y coordinate plotting routines described in Berger's, "Computer Graphics with Pascal," 1989. The calculations are affected by the presence of a blank lane subtraction flag which is set in the utilities module. Blank lane subtraction is performed on the data if the flag value is set to true (single or double) otherwise no subtraction is performed. The blank lane to be subtracted is designated in the data description module.

The system then allows the user to interactively set the baseline for the curve. Baseline setting is done by moving the left and right endpoints of a graphically displayed line on the video screen. Once the baseline is set, the system calculates the peaks within this baseline and converts these peak locations to X, Y pixel coordinates on the video display. Peaks are calculated in two major steps. First a wide peak is calculated, and then the smaller peaks are identified.

Six steps are necessary for finding the wide peak. They happen sequentially, gradually refining the wide peak location. Using the left and right baseline coordinates, a peak window is calculated. The baseline window is calculated by subtracting the right baseline from the left baseline. Next, a global mean value is calculated by summing all data values in the baseline window and dividing by the number of values. A weighted Global Mean Value is then found. This is defined as the index of the mean data value for all those values in the baseline window which are greater than the global mean. The Peak Window Mean Value is then determined. This value is the index of the mean data value in the peak window centered on the index of the weighted global mean value. The peak window is an internal constant typically set at 100. The index of the mean data value for all those values in the peak window which are greater than the peak window mean value is found. This value is then verified to determine that it is a local maximum in the peak window. If it is not, the actual local maximum value is substituted.

After a wide peak has been located, the rest of the peaks can be found. The data array is scanned from the left baseline to the right baseline looking for small peaks. Four steps are involved in locating these peaks.

As the window moves through the array, the average for the window is calculated. Each window average value is compared to the average value of all the values on the left side of the window average value and also to the average value of all the values on the right side of the window average value. The window average value must exceed the left side and the right side average values by an internal tolerance constant for the window average value to be declared significant enough to be a peak. In addition to checking peak tolerance, the location of the proposed peak is checked against a proximity constant to determine if the peak is too close to the previously defined broad peak. The status (true or false) is then sent to the next module. If a valid peak is found, its position is calculated and stored in the peak array.

When the peaks have been calculated and displayed, the system allows the user to edit the peaks. Peaks can be deleted by indicating the number of the peak to delete. Peaks can be inserted by moving a graphics cursor to the desired position on the screen and pressing the key designated for the insert command.

The first two lanes of any gel are designated as the standard lanes. These lanes are used to determine whether the gel preparation is similar to the established standards. This analysis is facilitated by graphically depicting a calculated regression line, and the slope, intercept and goodness-of-fit values for the standard lanes. The equations for these values are shown below.

$$Y = (Slope*X) + Intercept$$

where $Y = \log$ (Base numbers) typically $(2 \rightarrow 4)$ $X =$ index locations in the data array typically $(1 \rightarrow 1500)$ $$Slope = \frac{n * \Sigma_{i=1,n}(X_i * Y_i) - (\Sigma_{i=1,n}(X_i) * \Sigma_{i=1,n}(Y_i))}{n * \Sigma_{i=1,n}((X_1)^2) - (\Sigma_{i=1,n}(X_i) * \Sigma_{i=1,n}(X_i))}$$

where n = the number of values $$Intercept = \frac{\Sigma_{i=1,n}(Y_i)}{n} - \frac{Slope * \Sigma_{i=1,n}(X_i)}{n}$$

$$Y \text{ (mean value)} = \frac{\Sigma_{i=1,n}(Y_i)}{n}$$

$$R2 = \frac{\Sigma((\text{Regression value} - Y \text{ (mean value)})^2)}{\Sigma((\text{Actual value} - Y \text{ (mean value)})^2)}$$

where R2 = goodness of fit.

The system will generate four different curves for each of the remaining lanes (lanes 3 through n). The first graph is simply the unsmoothed raw data curve. The second graph is the smoothed curve. The third graph is the smoothed curve with the peaks labeled. The final plot is a graph of the smoothed curve overlaid by a graph of the relative cumulative percent of the total milliabsorption units. The graph also shows the values and location of the peak, $\overline{Sn}$, $\overline{Sw}$, $\overline{Sz}$, D and Z.

The $\overline{Sn}$, represents the number average which is derived from osmometry and is based on the number of molecules present. It is calculated as follows:

$$\overline{Sn}_. = \Sigma_{i=1,n}(V_i - B_i)/\Sigma_{i=1,n}((V_i - B_i)/\text{Log}(V_i))$$

$\overline{Sw}$, represents the weight average which is derived from the phenomenon of light scattering. The intensity of light scattered is proportional to the square of the size of the molecule. Mathematically, this is expressed as a product of the number of particles and the square of the molecular weight. The equation for the weight average is shown below.

$$\overline{Sw}_. = \Sigma_{i=1,n}((V_i - B_i)*\text{Log}(V_i))/\Sigma_{i=1,n}(V_i - B_i)$$

The $\overline{Sz}$, value represents the spacial relationships of polymer behavior under varying equilibrium conditions. In an ultracentrifuge, an equilibrium is reached when a polymer is distributed over the length of a cell in the ultracentrifuge. This equilibrium is dependent on both molecular weight and the molecular weight distribution of the polymer. The Sz equation is as follows.

$$\overline{Sz}_. = \Sigma_{i=1,n}((V_i - B_i)/\text{Log}(V_i)^2)/\Sigma_{i=1,n}((V_i - B_i)*\text{Log}(V_i))$$

D represents polydispersity which is the ratio of the weight Sw to the number average Sn. It is used to describe the breadth of the distribution, which may be very narrow to very wide. A polymer distribution of 1 is said to be monodispersed. Branched polymers, which are very cross-linked, can have a polydispersity between 20 and 50 because of the high potential for free radical polymerization chain extension and termination which leads to wide distributions.

$$D = \overline{Sw}/\overline{Sn}$$

Z is a measure of skewness and is the ratio of spacial relationships Sz to the number averages Sn. Z is affected by the predominance of high or low molecular polymer present.

$$Z = \overline{Sw}/\overline{Sn}$$

There are several reports that can be generated by this system. These reports are the various text and graphic files that There are several reports that can be generated by this system. These reports are the various text and graphic files that are created in the system modules and stored in files. These files are:
Original curve (Binary)
Smoothed curve (Binary)
Final plot (Binary)
  Lanes 1→2-regression line
  Lanes 3→n-relative/cumulative
Calibration data (ASCII)
Outlier list (ASCII)
Lane name files (ASCII)
Raw data as received from LKB (ASCII)
Raw data for a single lane (ASCII)
Decoded data (ASCII)

According to the method of this invention, the characteristics of a polynucleotide are determined by the interpretation of a continuous distribution of many lengths of biopolymer (RNA or DNA).

The characteristics described are number average molecular size, weight average molecular size, Z average molecular size, polydispersity and skewness.

The equation for number average molecular weight is:

$$\overline{M_n} = \frac{\sum_{i=1}^{\infty} N_i M_i}{\sum_{i=1}^{\infty} N_i} \qquad \text{Equation 1}$$

Assuming that absorbance is directly proportional to the weight of RNA loaded on the gel, then:

$$\Sigma W_i = \Sigma N_i M_i = \Sigma k A_i \qquad \text{Equation 2}$$

where k is a constant that relates absorbance to weight.

Making the substitution for weight defined in terms of absorbance into equation 1 yields:

$$\overline{M_n} = \frac{k \Sigma A_i}{k \Sigma A_i/M_i} \qquad \text{Equation 3}$$

Substitute the size, $S_i$, in bases, in for molecular weight in these polymer characterization equations. The final form of the number average molecular weight formula is equation 4.

$$\overline{Sn} = \frac{\Sigma A_i}{\Sigma A_i/S_i} \qquad \text{Equation 4}$$

This final substitution converts the formula from a weight relationship (gram/mole) to a size relationship (bases/mole) for application to this invention.

Weight Average Molecular Weight

The equation for weight average molecular weight is $$M_n = \frac{\Sigma N_i M_i^2}{\Sigma N_i M_i} \qquad \text{Equation 5}$$

Making the substitution for molecular weight with size yields:

$$Sw = \frac{\Sigma A_i S_i}{\Sigma A_i} \qquad \text{Equation 6}$$

Z Average Molecular Weight

The equation for Z average molecular weight is:

$$M_z = \frac{\Sigma N_i M_i^3}{\Sigma N_i M_i^2} \qquad \text{Equation 7}$$

Making the substitution of size in for molecular weight yields:

$$Sz = \frac{\Sigma A_i S_i^2}{\Sigma A_i S_i} \qquad \text{Equation 8}$$

Polydispersity and Skewness

Polydispersity is expressed as a simple ratio between number average and weight average molecular size.

$$D = \frac{\overline{S_w}}{\overline{S_n}} \qquad \text{Equation 9}$$

Skewness is expressed as a simple ratio between Z average and number average molecular size.

$$Z = \frac{\overline{S_z}}{\overline{S_n}} \qquad \text{Equation 10}$$

The use of the LKB Pharmacia UltroScan XL Laser Densitometer is outlined in the operating manuals of this instrument. A destained gel or clean, dry photographic negative of the gel can be scanned on the densitometer. After the scanning parameters have been set-up on the densitometer, raw data is collected from the serial port of this instrument and sent to an IBM-compatible computer for analysis with the newly designed software. A subroutine was written to read the data from the serial port of the densitometer and convert the data file into ASCII, a readable form of the data.

After the raw data is collected, it is converted into absorbance data files for further analysis. Interactive baseline assignment and peak addition and deletion are applied to these files to present the data in its final form. Three curves are presented at the conclusion of the data workup. The Original Curve is the raw data. The raw data is smoothed once and presented as the Smoothed Curve. The Relative Cumulative % Curve is calculated by the program and also contains the molecular size number average, weight average, Z average, polydispersity and skewness values. An example of this last curve is shown in FIG. 2.

Other features of the program include both single and double lane background correction of the gels, individual labelling of data files and an automatic internal calibration curve based upon a series of 14 RNA markers located in the first two lanes of the gel.

ALGORITHMS

Background correction of the gels was a primary function of this program. There were two types of correction; single, and double lane. The single lane algorithm was dependent upon the user to scan an empty lane on the gel and to name the lane BLANK when creating the file for lane names. This algorithm did a point-by-point subtraction of the absorbance values found in the specified sample lanes minus those in the blank lane. The double lane correction required blank lanes on either side of the sample lane. No lanes had to be identified as BLANK in the file for lane names; the algorithm "knew" to look at the lanes on either side of the sample. An average background was determined for the two blank lanes and then this was subtracted from the specified sample lane.

Another primary function of the program was the ability to search each lane of gel data and find the point which represented the peak maximum. The peak maximum algorithm searched for the highest absorbance value present in the data and then automatically assigned that value as peak maximum. The user had the opportunity to change that value through an interactive add/delete subroutine presented after the initial assignment was made. There were always two peak-finding algorithms in action; one for broad peak and one for narrow peak searching. The broad peak-finder was used for sample lanes where the computer had to find the peak maximum of a wide distribution. The narrow peak-finder was used for the RNA marker lanes, where 6 to 8 peaks had to be assigned a maximum. The peak maximums for the standards correlated to the distance they migrated into the gel. These values were used to set up an internal calibration curve based upon log size of the RNA marker versus distance migrated in millimeters.

The smoothing algorithm was required for the peak-finding algorithm to function properly. Raw data from the laser densitometer was jagged and needed to be smoothed or the narrow peak finder would have treated each spike in the data as a peak. The commands for the smoothing algorithm were:
1. sum the first/next 11 raw data points
2. determine the mean of those points
3. assign the mean as the first/next smoothed data point
4. increment the series of raw data points by +1
5. repeat the calculation Some data is lost when the smoothing algorithm takes place, however, this function was performed only once on each lane of data.

After the smoothing and background algorithms, a searching subroutine for outliers was automatically performed on the data. Based on the previous data point, an upper and lower limit was assigned to the next data point. If it fell outside these limits, the point was force fitted back to the y-position (mAUFS) of the previous data point, so that it would fit on the curve. The user had the choice to adjust the sensitivity of the searching program. Each time a point was identified as an outlier, it was flagged and its new position was listed on the CRT.

Once the baseline was assigned by the user, the area under the curve was integrated by another algorithm using the summation of area slices, which were then squared or cubed for the appropriate molecular weight equation.

EXAMPLE 1

Single-stranded RNA (ssRNA), i.e., a heteropolymer of single-stranded Poly (C,U) was synthesized by polymerization of nucleotide diphosphates with polynucleotide phosphorylase. The conditions for polymerization were 24° C. and pH 9.0. Viscosity was allowed to peak and plateau for maximum polymerization of the nucleoside diphosphates.

The biopolymer was then characterized using the method of the invention. Methods used to effect gel electrophoresis separations are well known in the art.

The following abbreviations are used:
MOPS = 3- (N-Morpholino) propanesulfonic acid
EDTA = Ethylenediaminetetraacetic acid The definition of buffers referred to in the discussion are as follows:

Denaturing Buffer: A mixture of formaldehyde and formamide of proportions 1:3.

Loading Buffer: A solution containing 500 uL of glycerol, 400 uL of a 1% (w/v) solution of bromophenol blue and xylene cyanol FF, 62 uL of water and 38 uL of 26.3 mM EDTA.

Stock solutions of approximately 5 mg/mL of ssRNA were prepared in water. Aliquots from 10 to 20 uL of the stock solution were treated with 15 uL of denaturing buffer, heated at 65° C. for 15 minutes and then quenched on ice. To this was added 5 uL loading buffer. A 25 uL sample was applied to a gel.

Agarose gels were prepared at 1.5% concentration and contained 2M formaldehyde as a denaturant to limit the secondary structure of the RNA during electrophoresis. Submerged gel apparatus was selected for best reproducibility of gel results and ease of use. Gels were electrophoresed in a buffer comprised of 20 mM MOPS, 5 mM sodium acetate and 1 mM EDTA. After electrophoresis, the gels were stained in a solution of 2 ug/mL ethidium bromide for 10 minutes and destained overnight in distilled water. The finished gels were then photographed with UV fluorescence at 590 nm (excitation 340 nm). Black and white photographs were kept as a permanent record and the negatives were used for scanning laser densitometry.

The electrophoresis gels were calibrated with a set of 14 heteropolymer RNA markers supplied by Bethesda Research Laboratories. The markers were used for accurate interpretation and quantitation of the size distribution data. The markers ranged in size from 160 to 9500 bases and were linear when log size (of RNA marker) was plotted against the distance migrated in millimeters. The resulting distribution of the biopolymers is best seen in the example of FIG. 2 in which log size was plotted against the distance migrated in millimeters for Experiment 18A.

Polynucleotide phosphorylase quickly catalyzes the formation of very large, monodispersed polymer from the nucleotide diphosphates. This is accurately reflected in the data for polydispersity values from 1.00 to 1.5 shown in Table 1. As the polymerization continues, random chain scission takes place as a result of the alkaline process conditions described earlier. Polydispersity increases, as expected for the broadening distribution.

TABLE 1
SIZE DISTRIBUTION OF POLY (C,U) IN BASES

| Parameter | EXPERIMENT | | | | |
|---|---|---|---|---|---|
| | 2A | 6A | 10A | 14A | 18A |
| $\bar{S}_n$ | 11,242 | 10,254 | 6713 | 2169 | 1357 |
| $\bar{S}_w$ | 11,267 | 10,423 | 7597 | 3640 | 2472 |
| $\bar{S}_z$ | 11,292 | 10,587 | 8409 | 5314 | 3897 |
| D | 1.00 | 1.02 | 1.13 | 1.68 | 1.82 |
| Z | 1.00 | 1.03 | 1.25 | 2.45 | 2.87 |

EXAMPLE 2

Using a method similar to that described above in Example 1, the following size distribution analysis was made for a homopolymer of single-stranded Poly (I).

TABLE 2
SIZE DISTRIBUTION OF POLY (I) IN BASES

| Parameter | EXPERIMENT | | | | |
|---|---|---|---|---|---|
| | 5A | 7A | 9A | 11A | 13A |
| $\bar{S}_n$ | 8910 | 4460 | 2920 | 2350 | 1740 |
| $\bar{S}_w$ | 9100 | 5700 | 4900 | 4420 | 3670 |
| $\bar{S}_z$ | 9280 | 6840 | 6790 | 6550 | 5920 |
| D | 1.02 | 1.28 | 1.68 | 1.88 | 2.11 |
| Z | 1.04 | 1.53 | 2.33 | 2.79 | 3.40 |

There has thus been described a software method to convert densitometry data from electrophoresis gels and to size distribution data derived from classical polymer chemical parameters of number average molecular size, weight average molecular size, Z average molecular size, polydispersity and skewness. The method is seen to represent a relatively simple means of characterizing polynucleotides and the like.

What is claimed is:

1. A method of characterizing polydispersed, single-stranded or double-stranded polynucleotides according to their molecular size distribution comprising the steps of converting the polynucleotides to single-stranded polynucleotides, electrophoresing the single-stranded polynucleotides in a lane of a gel, staining the electrophoresed polynucleotides, forming an image of having an absorbance distribution related to the gel containing the stained polynucleotides, scanning the image of the gel lane to convert the electrophoresed polynucleotides into pixel-by-pixel representations of the absorbance Ai distribution of the electrophoresed polynucleotides, in terms of absorbance Ai and size Si, calculating the number average molecular size $\bar{S}_n$ of the polynucleotides distribution by the formula $$\bar{S}_n = \Sigma Ai / \Sigma Ai/Si$$

calculating the weight average molecular size $\bar{S}_w$ of the polynucleotides distribution by the formula $$\bar{S}_w = \Sigma Ai\, Si / \Sigma Ai$$

calculating the Z average molecular size $\bar{S}_z$ of the polynucleotides distribution by the formula $$\bar{S}_z = \Sigma Ai\, Si^2 / \Sigma Ai\, Si$$

thereby to characterize the polynucleotide by the criteria number average molecular size, weight average molecular size, and Z average molecular size.

2. The method set forth in claim 1 which includes the additional step of
calculating the polydispersity D of the polynucleotides distribution by the formula $$D = \bar{S}_w / \bar{S}_n.$$

3. The method set forth in claim 2 which includes the additional step of calculating the skewness Z of the polynucleotide distribution by the formula $$Z = \bar{S}_z / \bar{S}_n.$$

4. The method set forth in claim 1 which includes the additional step of calculating the skewness Z of the polynucleotide distribution by the formula $$Z = \bar{S}_z / \bar{S}_n.$$

5. The method of claim 1 which includes the additional step of forming a blank lane in the image alongside the image of the electrophoresed lane in the gel,
scanning the blank lane to obtain pixel-by-pixel representations of the absorbance of the blank lane,
subtracting pixel-by-pixel the absorbance of the blank lane from that of the electrophoresed lane before calculating.

6. The method set forth in claim 1 which includes the additional step of forming a blank lane in the image on either side of the image of the electrophoresed lane, scanning the blank lanes to obtain pixel-by-pixel representation of absorbance of each blank lane, averaging pixel-by-pixel the absorbance of the blank lanes, and subtracting pixel-by-pixel the absorbance of the average of the blank lanes from that of the electrophoresed lane before calculating.

7. The method set forth in claim 6 which includes the additional step of
calculating the polydispersity D of the polynucleotides distribution by the formula $$D = \bar{S}_w / \bar{S}_n;\ \text{and}$$

the additional step of calculating the skewness Z of the polynucleotide distribution by the formula $$Z = \bar{S}_z / \bar{S}_n.$$

8. The method set forth in claim 5 which includes the additional step of
calculating the polydispersity D of the polynucleotides distribution by the formula $$D = \bar{S}_w / \bar{S}_n;\ \text{and}$$

the additional step of calculating the skewness Z of the polynucleotide distribution by the formula $$Z = \bar{S}_z / \bar{S}_n.$$

9. The method set forth in claim 1 which includes the additional step of smoothing the scanned representations of absorbance by:

(a) summing the first/next eleven representations,
(b) determining the means of those representations,
(c) assign the mean as a first/next smoothed representation,
(d) increment the series of representations by one,
(e) repeat steps (a) through (d).

10. The method set forth in claim 5 which includes the additional step of forming a blank lane in the image alongside the image of the electrophoresed lane in the gel,
   scanning the blank lane to obtain pixel-by-pixel representations of the absorbance of the blank lane,
   subtracting pixel-by-pixel the absorbance of the blank lane from that of the electrophoresed lane before calculating.

11. The method set forth in claim 6 which includes the additional step of forming a blank lane in the image alongside the image of the electrophoresed lane in the gel,
   scanning the blank lane to obtain pixel-by-pixel representations of the absorbance of the blank lane,
   subtracting pixel-by-pixel the absorbance of the blank lane from that of the electrophoresed lane before calculating.

* * * * *